United States Patent [19]

Swanson

[11] 4,158,893

[45] Jun. 26, 1979

[54] PROTECTIVE SLEEVE FOR IMPLANTABLE PROSTHESIS AND METHOD OF PROTECTING THE PROSTHESIS

[76] Inventor: Alfred B. Swanson, 2945 Bonnell, SE., Grand Rapids, Mich. 49506

[21] Appl. No.: 731,825

[22] Filed: Oct. 12, 1976

[51] Int. Cl.$^2$ .............................................. A61F 1/24
[52] U.S. Cl. .................... 3/1.91; 128/92 C
[58] Field of Search .................. 3/1.9–1.913; 128/92 C, 92 CA

[56] References Cited

U.S. PATENT DOCUMENTS

| 3,744,061 | 7/1973 | Frost .................... 128/92 CA X |
| 3,816,854 | 6/1974 | Schlein ......................... 128/92 C |
| 3,820,167 | 6/1974 | Sivash ............................. 3/1.912 |
| 3,875,594 | 4/1975 | Swanson .................. 128/92 C X |
| 3,924,274 | 12/1975 | Heimke et al. ................. 3/1.91 |
| 3,992,725 | 11/1976 | Homsy ............................. 3/1.9 X |
| 4,012,796 | 3/1977 | Weisman et al. .................. 3/1.91 |

FOREIGN PATENT DOCUMENTS

| 2154338 | 5/1973 | Fed. Rep. of Germany ............ 3/1.911 |
| 2253338 | 5/1974 | Fed. Rep. of Germany ............... 3/1.9 |
| 2545821 | 4/1976 | Fed. Rep. of Germany ............ 3/1.911 |
| 1443470 | 7/1976 | United Kingdom .................... 3/1.9 |

Primary Examiner—Ronald L. Frinks
Attorney, Agent, or Firm—Price, Heneveld, Huizenga & Cooper

[57] ABSTRACT

A protective device for a surgically implantable prosthesis having a pair of outwardly directed intramedullary stem portions, includes an elongated, one-piece sleeve defining a passage for receipt of one of said stem portions and insertable within one of the intramedullary canals of the bones adjacent the joint. The sleeve has an end portion extending from the canal and protecting the implant from lacerations or tearing by the edges of the bone.

15 Claims, 2 Drawing Figures

PROTECTIVE SLEEVE FOR IMPLANTABLE PROSTHESIS AND METHOD OF PROTECTING THE PROSTHESIS

BACKGROUND OF THE INVENTION

This invention relates to surgically implantable prosthetic joints and more particularly to a unique device for and a method of protecting such joints from lacerations or tearing caused by contact with the edges of adjacent bones and protect bone from fracture.

Heretofore various surgically implantable prosthetic devices have been proposed for replacing bone joints. Typically, the prosthesis includes a midsection and a pair of outwardly directed stem portions. The stem portions correspond generally to the dimensions of the intramedullary canals of the bones adjacent the joint and are implanted within the canals. Examples of such prosthetic joints may be found in Applicant's prior U.S. Pat. No. 3,462,765, issued Aug. 26, 1969 and entitled SURGICALLY IMPLANTABLE PROSTHETIC JOINT and in Applicant's prior U.S. Pat. No. 3,875,594 issued Apr. 8, 1975 and entitled SURGICALLY IMPLANTABLE PROSTHETIC JOINT HAVING LOAD DISTRIBUTING FLEXIBLE HINGE.

Prosthetic joints of the type disclosed in the aforementioned patents are fabricated from flexible elastomeric, physiologically inert material. These flexible, one-piece joints have been widely used and have improved markedly the prognosis for restruction patients. The devices illustrated in these patents have utility in replacement of finger joints in a human hand and also may be used to replace various other joints of the human body.

Clinical experience and mechanical testing programs have indicated that the flex life of these flexible implants is essentially infinite unless a laceration occurs on the surface. If a laceration or tear of the surface of a prosthesis should occur, tear propagation throughout the device will usually result. This tear propagation can and has resulted in fracture of the prosthesis after implantation. Various causes for such lacerations or tearing of the surface have been hypothesized. For example, the damage to or fracture of the prosthesis may be the result of insufficient bone resection or an irregularity of the edges of the resected bone.

Also, with certain types of patients, especially those suffering from severe rheumatoid arthritis, fractures are more prevalent. Rheumatoid arthritis produces alterations of the bone and tendon balance of the joints and further plays an important role in the mechanism of reconstructed joints. The bones of these patients may become thin and atrophied and the edges of the bones at the joint may become very sharp. Sublaxation of the joint bones results in impingement of the sharp bone edges on the midsection of the implant and subsequent lacerations or tears. An implant may exert sufficient pressure to result in fracture of the bones themselves with these patients. As a result, these patients may be denied the benefits of such corrective procedures.

A need, therefore, exists for a device for and a method of protecting the flexible elastomeric prosthetic joint from lacerations or tearing and subsequent fracture resulting from impingement on the prosthesis by sharp bone edges adjacent the joint.

SUMMARY OF THE INVENTION

In accordance with the present invention, a unique protective device and method of using same is provided whereby the problems heretofore experienced with fracturing of a surgically implantable prosthesis or of the bones adjacent the joint are substantially eliminated. Essentially, the protective device comprises an elongated sleeve which defines a passage for receipt of one of the stem portions of the prosthesis. The sleeve is surgically implantable within one of the intramedullary canals of the bone adjacent the joint and includes a protective end portion which extends from the canal and prevents impingement on the joint by the edges of the resected bone.

In narrower aspects of the invention, the protective device includes a fluted end portion which is circumferentially flared or curved outwardly and the sleeve is approximately one-third the length of the intramedullary stem portions of the prosthesis. Further, the exterior surface in cross section of the protective sleeve is preferably rectangular to prevent rotation within the intramedullary canal thereby providing lateral and rotational stability. The sleeve may be fabricated from a medical grade material which permits bone ingrowth into the exterior surface thereof or, in the alternative, the sleeve may be bonded to the interior surface of the intramedullary canal.

The method of protecting the surgically implantable prosthesis in accordance with the present invention contemplates the forming of a sleeve including the protective end portions and surgically implanting the sleeve in each of the intramedullary canals prior to surgical implantation of the stem portions of the prosthetic device.

DETAILED DESCRIPTION OF THE PREFERRED EMBODIMENT

Figure 1:
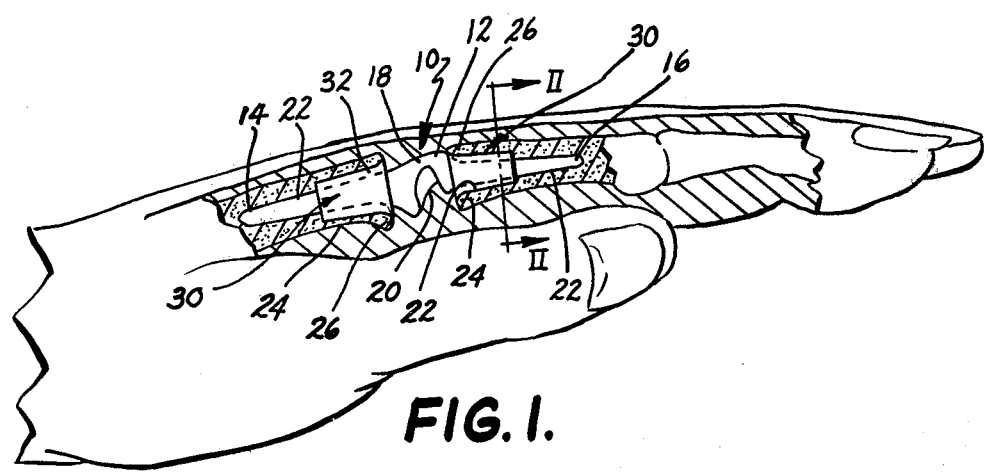
FIG. 1 is a partial cross section of a human hand showing the protective device and a prosthetic joint in accordance with the present invention in place.

With reference to the drawings, FIG. 1 illustrates the placement of a flexible implant for the knuckle and finger joint in a human hand. The implant, generally designated 10 includes an enlarged midsection 12 and a pair of outwardly extending stem portions 14, 16. The prosthesis 10 includes a rounded thickened section 18 along the upper or dorsal surface of the enlarged midsection and a transverse trough or channel 20 formed in the lower or volar surface of the enlarged midsection. For a more detailed description of the implant, reference may be had to Applicant's aforementioned U.S. Pat. No. 3,875,594. The implant is of the type sold by Dow Corning under the Trademark SILASTIC Finger Joint Implant.

During the implantation procedure, the natural joint is partially, surgically removed and the intramedullary canals 22 of the adjacent bone ends 24 are prepared with a curad, broach or drill to receive the stem portions of the prosthesis. With certain patients, especially those suffering from rheumatoid arthritis, as previously stated, the edges 26 of the bones 24 adjacent the joint may become very sharp or ragged. These sharp edges have a tendency to impinge on the midsection 12 of the prosthesis resulting in lacerations or tearing of the upper and lower surfaces thereof. Unless this impingement is prevented, fracture of the prosthetic joint may occur. Also, the thin bones are themselves subject to fracture.

Figure 2:
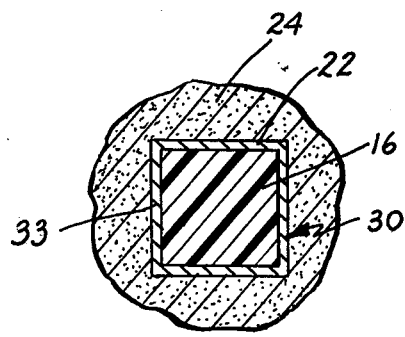
FIG. 2 is an enlarged fragmentary, cross-sectional view taken along line II—II of FIG. 1.

In accordance with the present invention, a protective device 30 in the form of a sleeve is surgically implanted within the intramedullary canal prior to implantation of the stem portions of the joint. The sleeves 30 have the same general shape as the stem portions 14, 16 of the implant and each defines a central passage for receipt of the implant (FIG. 2). The end portion 32 of the sleeve is fluted or flared radially outwardly around its circumference so as to be between the bone edges and the prosthesis 10 when both are in place. The protective sleeve prevents impingement of the midsection 12 of the joint by the potentially sharp edges of the bones adjacent the joint. Also, the sleeve reinforces the bone structure and helps in preventing bone fracture.

As best seen in FIG. 2, it is preferred that the exterior surface 33, in cross section, of the protective sleeve be of a generally rectangular shape. This shaping of the protective sleeve prevents rotation of the sleeve providing lateral and rotational stability to the restructured joint. The interior surface of the protective sleeve is formed with the same general exterior shape of the implant stem portion (FIG. 2). As stated in the aforementioned U.S. Patents, it is preferred that the stem portions of the prosthetic device also be generally rectangular in shape.

The protective sleeve may be fabricated from a medical grade material which permits the bone to grow into its exterior surface but still permits movement between the implant exterior surface and the interior surface of the sleeve. One such material would be porous polytetrafluoroethylene. An alternative to the use of a material which permits bone ingrowth would be the use of a high density polyethylene material or other such plastic material coated with a bone ingrowth medium. The sleeve may also be cemented within the intramedullary canal.

The wall thickness of the sleeve would vary with the particular size implant and with the physical dimensions of the bones adjacent the restructured joint. For example, if the bone and canal dimensions of the particular patient indicated use of a No. 8 size Dow Corning SILASTIC finger joint implant, a No. 7 size would be used in conjunction with the sleeve. The sleeve thickness would be selected to reduce the dimensions of the intramedullary canal to provide a proper fit for this next lower sized implant. It is presently preferred that the sleeve have a length approximately one third the length of the stem portions of the implant. In any event, the primary consideration is to line or cover the exterior surface of the bone edges and the immediate interior surface of the intramedullary canals. The device in accordance with the present invention allows motion to occur at the new interface, namely, between the implant and the sleeve is opposed to motion between the implant and the bone. The sleeve, therefore, functions to protect the bone from excessive stress and may also serve as a weight or load bearing area.

Although the protective device and method of using same has been discussed and illustrated primarily with reference to the replacement of the joints of the fingers, the device also has utility in replacement of other joints of the human body. The device is usable in any situation where there is danger of impingement on a prosthesis by sharp bone edges.

As should now be readily apparent, the unique protective device and method of protecting a surgically implantable prosthesis, in accordance with the present invention, eliminates or substantially reduces the occurrence of fracture of a silicone rubber or other flexible implant which has heretofore resulted from impingement on the device by the sharp or potentially sharp edges of adjacent bones. The present invention substantially increases the prognosis for restruction patients, especially those suffering from severe rheumatoid arthritis. The thickened or fluted and flared portion of the sleeve besides protecting the prosthetic joint, also serves as a load bearing area protecting the bones. The sleeve presents a new interface at which the stem portions of the implant may slide or reciprocate thereby reducing stress on the bones. The sleeve could be formed by any clinically inert material having sufficient strength to prevent impingment by the bony edges on the implant.

Those skilled in the art will readily appreciate the many advantages of the present invention which have not heretofore been obtainable. Those so skilled may also recognize that modifications may be made and it is expressly intended that the equivalent arrangements be covered unless the following claims by their wording, expressly state otherwise.

The embodiments of the present invention in which an exclusive property or privilege is claimed are defined as follows.

1. A protective device for a flexible surgically implantable prosthesis used in replacing knuckle bone joints, the prosthesis being of the type having at least one outwardly directed stem portion, corresponding generally to the dimensions of the intramedullary canal of a bone adjacent said joint for implantation therein, said device comprising:

an elongated one-piece member defining a passage for receipt of said stem portion of said prosthesis, said member being insertable within said intramedullary canal and including a protective end portion dimensioned to extend adjacent the open end of said canal and to cover the exterior surface of the bone edge to protect said prosthesis from impingement by the end of said bone said protective device being fabricated from a material permitting reciprocating movement between the stem of the prosthesis and the interior surface of the protective device.

2. A protective device as defined by claim 1 wherein said protective end portion comprises a fluted portion, flared radially outwardly around the circumference of the member to prevent laceration of said prosthesis by said bone end.

3. A protective device as defined by claim 2 wherein said member has a rectangular exterior surface in cross section to prevent rotation within said intramedullary canal.

4. A protective device as defined by claim 3 wherein said member has an interior surface in cross section corresponding to the exterior surface of said stem portion of said prosthesis.

5. A protective device as defined by claim 4 wherein said material is a porous polytetrafluoroethylene.

6. A protective device as defined by claim 4 wherein said material is a high density polyethylene.

7. A protective device as defined by claim 4 wherein said member is a sleeve and said sleeve has a length equal to approximately one-third the length of the stem portion of said prosthesis.

8. In combination, a protective device and a surgically implantable flexible prosthesis used in replacing bone joints and the like, said prosthesis being of the type having at least one outwardly directed stem portion, corresponding generally to the dimensions of the intramedullary canal of a bone adjacent said joint for implantation therein, said protective device comprising:

a one-piece member defining a passage receiving said stem portion of said prosthesis, said member being insertable within said intramedullary canal and including a protective end portion dimensioned to extend adjacent the open end of said canal and to cover the exterior surface of the bone edge to protect said prosthesis from impingement by the end of said bone, and said stem portion and said member being sized relative to one another and being of such materials to permit sliding, reciprocating movement of said stem relative to said member subsequent to implantation of said prosthesis thereby protecting the bone from excessive stress.

9. A method of protecting a flexible surgically implantable prosthesis used in replacing bone joints and the like, from lacerations and tears caused by contact with the bone edges, the prosthesis being of the type including a midsection and at least one outwardly extending stem portion, the stem portion being insertable into the intramedullary canal of a bone adjacent the joint, comprising the steps of:

forming a member defining a passage dimensioned for receipt of one of said stem portions;

surgically implanting said member within said intramedullary canal prior to insertion of said stem portion and positioning said member so that the end portion thereof is between the bone edge and said prosthesis and covers said bone edge when said prosthesis is implanted.

10. A method as defined by claim 9 wherein said member has a generally rectangular exterior surface in cross section.

11. A method as defined by claim 10 including the step of forming said member with a fluted end portion, flared radially outwardly around the circumference of said member.

12. A method as defined by claim 11 wherein said member is formed from a material which permits bone ingrowth into the exterior surface thereof.

13. A method as defined by claim 12 wherein said material is a medical quality, porous polytetrafluoroethylene.

14. A method as defined by claim 11 wherein said member is formed from a high density polyethylene.

15. A method as defined by claim 14 further including the step of bonding the exterior surface of said member to the intramedullary canal.

* * * * *